US012596247B2

(12) United States Patent
Zare Seisan

(10) Patent No.: US 12,596,247 B2
(45) Date of Patent: Apr. 7, 2026

(54) PRESCRIPTION SYSTEM FOR FLEXIBLE LENSES

(71) Applicant: Snap Inc., Santa Monica, CA (US)

(72) Inventor: Farid Zare Seisan, San Diego, CA (US)

(73) Assignee: SNAP INC., Santa Monica, CA (US)

( * ) Notice: Subject to any disclaimer, the term of this patent is extended or adjusted under 35 U.S.C. 154(b) by 843 days.

(21) Appl. No.: 17/697,477

(22) Filed: Mar. 17, 2022

(65) Prior Publication Data

US 2023/0296877 A1 Sep. 21, 2023

(51) Int. Cl.
| | |
|---|---|
| *G02B 26/00* | (2006.01) |
| *A61B 3/00* | (2006.01) |
| *A61B 3/028* | (2006.01) |
| *G02B 26/08* | (2006.01) |
| *G06F 3/16* | (2006.01) |

(52) U.S. Cl.
CPC .......... *G02B 26/004* (2013.01); *A61B 3/0025* (2013.01); *A61B 3/028* (2013.01); *G02B 26/0875* (2013.01); *G06F 3/167* (2013.01)

(58) Field of Classification Search
CPC .... G02B 26/004; G02B 26/0875; G02B 3/14; G02B 27/017; A61B 3/0025; A61B 3/028; A61B 3/0033; A61B 3/0041; A61B 3/04; G06F 3/167; G02C 7/027; G02C 7/085
USPC ....................................... 351/246
See application file for complete search history.

(56) References Cited

U.S. PATENT DOCUMENTS

| | | | |
|---|---|---|---|
| 5,440,357 | A | 8/1995 | Quaglia |
| 2018/0136486 | A1 | 5/2018 | Macnamara et al. |
| 2019/0212546 | A1 | 7/2019 | Sohn et al. |
| 2019/0243123 | A1 | 8/2019 | Bohn |
| 2019/0369353 | A1 | 12/2019 | Franklin et al. |
| 2020/0096770 | A1 | 3/2020 | Pedder et al. |

FOREIGN PATENT DOCUMENTS

| | | |
|---|---|---|
| CN | 118871839 A | 10/2024 |
| FR | 2787204 | 6/2000 |

(Continued)

OTHER PUBLICATIONS

Optical System for Wide Angle Camera With Aspheric Surface, Myeongjae Noh; KR200406967 (Year: 2006).*

(Continued)

*Primary Examiner* — Bumsuk Won
*Assistant Examiner* — Rahman Abdur
(74) *Attorney, Agent, or Firm* — SCHWEGMAN LUNDBERG & WOESSNER, P.A.

(57) ABSTRACT

Systems and methods herein describe a prescription system for flexible lenses. The prescription system receives a current state of a pair of flexible lenses of a pair of eyeglasses, causes presentation of one or more images on a graphical user interface displayed on the lenses, receives audio feedback relating to the one or more images from a wearer of the eyeglasses, based on the feedback, sends an instruction to cause an air pump affixed to the eyeglasses to inflate one or more compartments of the pair of lenses, in response to the instruction, receives an updated state of the pair of flexible lenses, and generates prescription data for the pair of lenses based on the updated state of the pair of lenses.

19 Claims, 7 Drawing Sheets

(56)     References Cited

FOREIGN PATENT DOCUMENTS

| WO | 2016115285 | 7/2016 |
| WO | 2023177721 | 9/2023 |

OTHER PUBLICATIONS

"International Application Serial No. PCT/US2023/015270, International Search Report mailed Jun. 28, 2023", 5 pgs.

"International Application Serial No. PCT/US2023/015270, Written Opinion mailed Jun. 28, 2023", 9 pgs.

"International Application Serial No. PCT/US2023/015270, International Preliminary Report on Patentability mailed Sep. 26, 2024", 11 pgs.

"European Application Serial No. 23715662.5, Response to Communication pursuant to Rules 161 and 162 EPC filed Apr. 25, 2025", 8 pgs.

"European Application Serial No. 23715662.5, Communication Pursuant to Article 94(3) EPC mailed Dec. 22, 2025", 5 pgs.

* cited by examiner

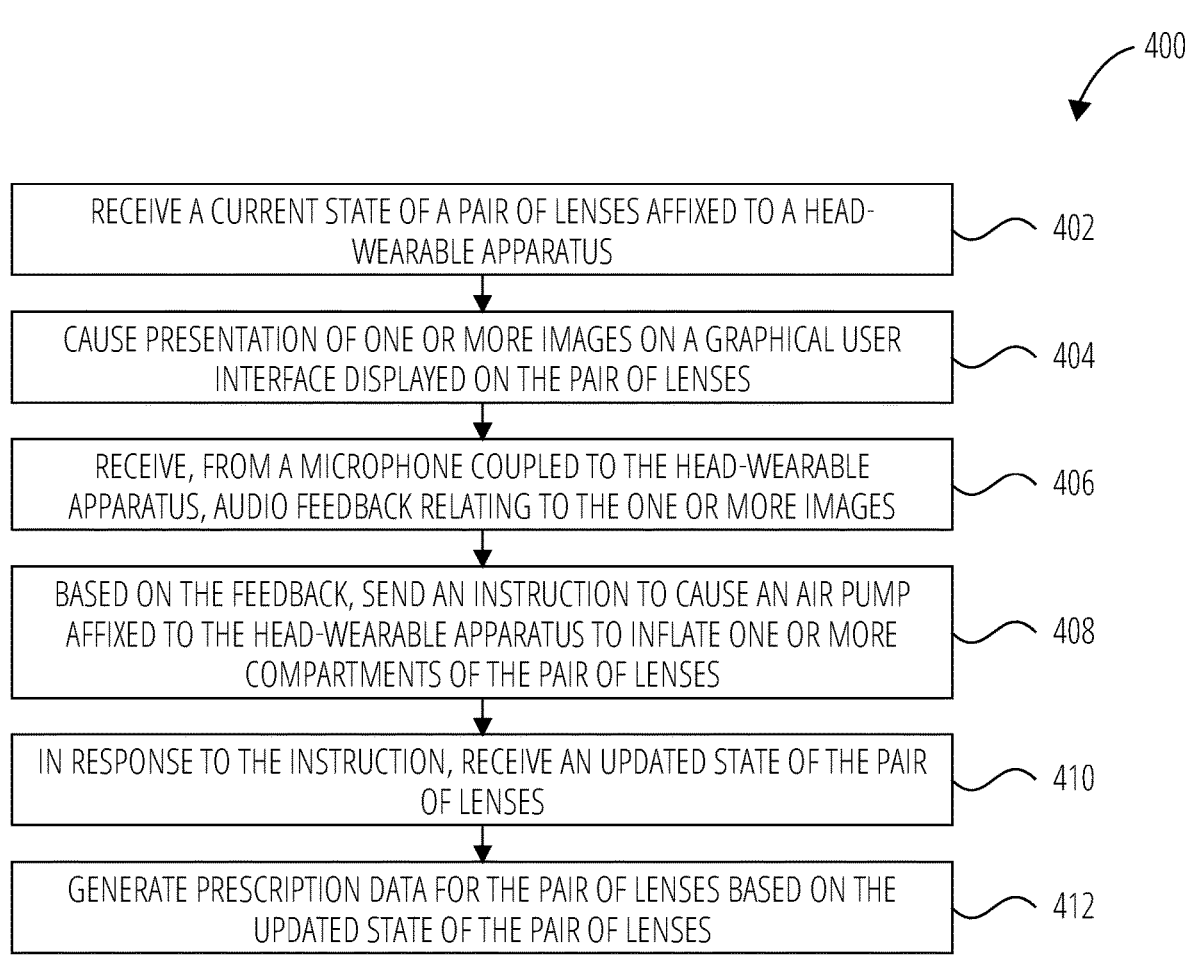

400

RECEIVE A CURRENT STATE OF A PAIR OF LENSES AFFIXED TO A HEAD-WEARABLE APPARATUS — 402

CAUSE PRESENTATION OF ONE OR MORE IMAGES ON A GRAPHICAL USER INTERFACE DISPLAYED ON THE PAIR OF LENSES — 404

RECEIVE, FROM A MICROPHONE COUPLED TO THE HEAD-WEARABLE APPARATUS, AUDIO FEEDBACK RELATING TO THE ONE OR MORE IMAGES — 406

BASED ON THE FEEDBACK, SEND AN INSTRUCTION TO CAUSE AN AIR PUMP AFFIXED TO THE HEAD-WEARABLE APPARATUS TO INFLATE ONE OR MORE COMPARTMENTS OF THE PAIR OF LENSES — 408

IN RESPONSE TO THE INSTRUCTION, RECEIVE AN UPDATED STATE OF THE PAIR OF LENSES — 410

GENERATE PRESCRIPTION DATA FOR THE PAIR OF LENSES BASED ON THE UPDATED STATE OF THE PAIR OF LENSES — 412

FIG. 4

PRESCRIPTION SYSTEM FOR FLEXIBLE LENSES

TECHNICAL FIELD

Embodiments herein generally relate to generating eyeglasses prescriptions. More specifically, but not by way of limitation, embodiments herein describe a prescription system for flexible eyeglass lenses.

BACKGROUND

Corrective lenses have two curvatures for correcting visions: cylindrical and spherical. The spherical curvature converges or diverges light into a single point. The cylindrical curvature converges or diverges light into a single plane. The spherical curvature indicates the amount of lens power that is prescribed to correct nearsightedness or farsightedness. The cylindrical curvature indicates the amount of lens power needed for astigmatism.

BRIEF DESCRIPTION OF THE SEVERAL VIEWS OF THE DRAWINGS

To easily identify the discussion of any particular element or act, the most significant digit or digits in a reference number refer to the figure number in which that element is first introduced.

FIG. 4 is a flowchart of a method for remotely adjusting the prescription of a pair of wearable eyeglasses, according to example embodiments.

DETAILED DESCRIPTION

Prescriptions are the result of modifying the front curvature and back curvature of a lens. Once a prescription is generated on a lens with inflexible curvatures, it is nearly impossible to modify the prescriptions. A person's prescription may change over time and purchasing new eyeglasses with a new prescription each time is expensive. People who are not physically proximate to an optometrist may not have the resources to visit an optometrist and would be unable to obtain prescription glasses.

Systems and methods herein describe a prescription system for flexible lenses. The flexible lenses replace traditional lenses by using a soft material that can expand and shrink using air pressure. Each flexible lens on a pair of eyeglasses includes a front soft lens and back soft lens that are separated by a hard lens. The soft lens is made of a flexible material such as plastic. The hard lens is made of an inflexible material such as a clear glass or high-index plastic that does not bend light. A pump and vacuum system is attached to each flexible lens and pumps air in and out of the gaps between the soft lenses and the hard lens, which results in curvature changes of the soft lenses. This will generate concave or convex lenses with a prescription.

The pump and vacuum system is controlled using a software interface (e.g., a prescription system). The prescription system manipulates the flexible lenses on a pair of eyeglasses by leveraging augmented reality/virtual reality (AR/VR) software installed on the pair of eyeglasses. For example, the prescription system causes display of an augmented reality image on each flexible lens of the pair of eyeglasses. The prescription system receives feedback from a user of the eyeglasses (e.g., via a microphone coupled to the eyeglasses) and modifies the curvature of the flexible lenses until the user of the eyeglasses can see the images with their preferred level of clarity. The prescription system converts the curvature measurements of the flexible lenses (e.g., using a spherometer and pressure gauges coupled to the eyeglasses) into a prescription. The generated prescription can be applied to any pair of eyeglasses (e.g., traditional eyeglasses). Further details of the prescription system and flexible lenses are described below.

Networked Computing Environment

Figure 1:
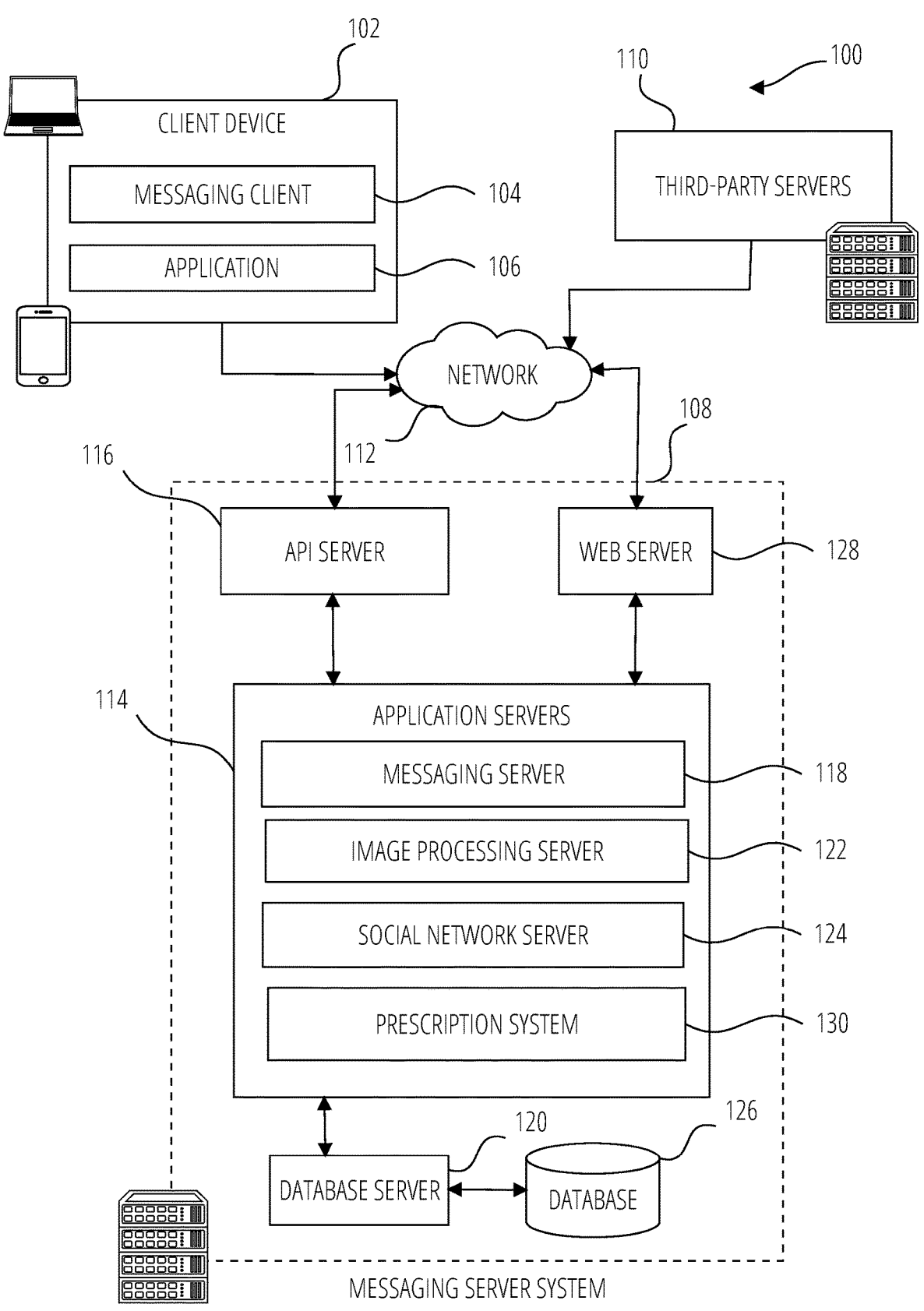
FIG. 1 is a block diagram showing an example messaging system for exchanging data over a network.

FIG. 1 is a block diagram showing an example messaging system 100 for exchanging data (e.g., messages and associated content) over a network. The messaging system 100 includes multiple instances of a client device 102, each of which hosts a number of applications, including a messaging client 104 and other applications 106. Each messaging client 104 is communicatively coupled to other instances of the messaging client 104 (e.g., hosted on respective other client devices 102), a messaging server system 108 and third-party servers 110 via a network 112 (e.g., the Internet). A messaging client 104 can also communicate with locally-hosted applications 106 using Applications Program Interfaces (APIs).

A messaging client 104 is able to communicate and exchange data with other messaging clients 104 and with the messaging server system 108 via the network 112. The data exchanged between messaging clients 104, and between a messaging client 104 and the messaging server system 108, includes functions (e.g., commands to invoke functions) as well as payload data (e.g., text, audio, video or other multimedia data).

The messaging server system 108 provides server-side functionality via the network 112 to a particular messaging client 104. While certain functions of the messaging system 100 are described herein as being performed by either a messaging client 104 or by the messaging server system 108, the location of certain functionality either within the messaging client 104 or the messaging server system 108 may be a design choice. For example, it may be technically preferable to initially deploy certain technology and functionality within the messaging server system 108 but to later migrate this technology and functionality to the messaging client 104 where a client device 102 has sufficient processing capacity.

The messaging server system 108 supports various services and operations that are provided to the messaging client 104. Such operations include transmitting data to, receiving data from, and processing data generated by the messaging client 104. This data may include message content, client device information, geolocation information, media augmentation and overlays, message content persistence conditions, social network information, and live event information, as examples. Data exchanges within the messaging system 100 are invoked and controlled through functions available via user interfaces (UIs) of the messaging client 104.

Turning now specifically to the messaging server system 108, an Application Program Interface (API) server 116 is coupled to, and provides a programmatic interface to, application servers 114. The application servers 114 are communicatively coupled to a database server 120, which facilitates access to a database 126 that stores data associated with messages processed by the application servers 114. Similarly, a web server 128 is coupled to the application servers 114 and provides web-based interfaces to the application servers 114. To this end, the web server 128 processes incoming network requests over the Hypertext Transfer Protocol (HTTP) and several other related protocols.

The Application Program Interface (API) server 116 receives and transmits message data (e.g., commands and message payloads) between the client device 102 and the application servers 114. Specifically, the Application Program Interface (API) server 116 provides a set of interfaces (e.g., routines and protocols) that can be called or queried by the messaging client 104 in order to invoke functionality of the application servers 114. The Application Program Interface (API) server 116 exposes various functions supported by the application servers 114, including account registration, login functionality, the sending of messages, via the application servers 114, from a particular messaging client 104 to another messaging client 104, the sending of media files (e.g., images or video) from a messaging client 104 to a messaging server 118, and for possible access by another messaging client 104, the settings of a collection of media data (e.g., story), the retrieval of a list of friends of a user of a client device 102, the retrieval of such collections, the retrieval of messages and content, the addition and deletion of entities (e.g., friends) to an entity graph (e.g., a social graph), the location of friends within a social graph, and opening an application event (e.g., relating to the messaging client 104).

The application servers 114 host a number of server applications and subsystems, including for example a messaging server 118, an image processing server 122, a social network server 124 and a prescription system 130. The messaging server 118 implements a number of message processing technologies and functions, particularly related to the aggregation and other processing of content (e.g., textual and multimedia content) included in messages received from multiple instances of the messaging client 104. As will be described in further detail, the text and media content from multiple sources may be aggregated into collections of content (e.g., called stories or galleries). These collections are then made available to the messaging client 104. Other processor and memory intensive processing of data may also be performed server-side by the messaging server 118, in view of the hardware requirements for such processing.

The application servers 114 also include an image processing server 122 that is dedicated to performing various image processing operations, typically with respect to images or video within the payload of a message sent from or received at the messaging server 118.

The social network server 124 supports various social networking functions and services and makes these functions and services available to the messaging server 118. Examples of functions and services supported by the social network server 124 include the identification of other users of the messaging system 100 with which a particular user has relationships or is "following," and also the identification of other entities and interests of a particular user.

The prescription system 130 generates eyeglasses prescriptions by remotely controlling a pair of eyeglasses with an AR/VR display system. For example, the prescription system 130 may project images onto the pair of eyeglasses and adjust the prescription of the pair of eyeglasses by manipulating the curvature of each lens of the eyeglasses using a pump and vacuum system.

Returning to the messaging client 104, features and functions of an external resource (e.g., an application 106 or applet) are made available to a user via an interface of the messaging client 104. In this context, "external" refers to the fact that the application 106 or applet is external to the messaging client 104. The external resource is often provided by a third party but may also be provided by the creator or provider of the messaging client 104. The messaging client 104 receives a user selection of an option to launch or access features of such an external resource. The external resource may be the application 106 installed on the client device 102 (e.g., a "native app"), or a small-scale version of the application (e.g., an "applet") that is hosted on the client device 102 or remote of the client device 102 (e.g., on third-party servers 110). The small-scale version of the application includes a subset of features and functions of the application (e.g., the full-scale, native version of the application) and is implemented using a markup-language document. In one example, the small-scale version of the application (e.g., an "applet") is a web-based, markup-language version of the application and is embedded in the messaging client 104. In addition to using markup-language documents (e.g., a .*ml file), an applet may incorporate a scripting language (e.g., a .*js file or a .json file) and a style sheet (e.g., a .*ss file).

In response to receiving a user selection of the option to launch or access features of the external resource, the messaging client 104 determines whether the selected external resource is a web-based external resource or a locally-installed application 106. In some cases, applications 106 that are locally installed on the client device 102 can be launched independently of and separately from the messaging client 104, such as by selecting an icon, corresponding to the application 106, on a home screen of the client device 102. Small-scale versions of such applications can be launched or accessed via the messaging client 104 and, in some examples, no or limited portions of the small-scale application can be accessed outside of the messaging client 104. The small-scale application can be launched by the messaging client 104 receiving from a third-party server 110, for example, a markup-language document associated with the small-scale application and processing such a document.

In response to determining that the external resource is a locally-installed application 106, the messaging client 104 instructs the client device 102 to launch the external resource by executing locally-stored code corresponding to the external resource. In response to determining that the external resource is a web-based resource, the messaging client 104 communicates with the third-party servers 110 (for example) to obtain a markup-language document corresponding to the selected external resource. The messaging client 104 then processes the obtained markup-language document to present the web-based external resource within a user interface of the messaging client 104.

The messaging client 104 can notify a user of the client device 102, or other users related to such a user (e.g., "friends"), of activity taking place in one or more external resources. For example, the messaging client 104 can provide participants in a conversation (e.g., a chat session) in the messaging client 104 with notifications relating to the current or recent use of an external resource by one or more members of a group of users. One or more users can be invited to join in an active external resource or to launch a recently-used but currently inactive (in the group of friends) external resource. The external resource can provide participants in a conversation, each using respective messaging clients 104, with the ability to share an item, status, state, or location in an external resource with one or more members of a group of users into a chat session. The shared item may be an interactive chat card with which members of the chat can interact, for example, to launch the corresponding external resource, view specific information within the external resource, or take the member of the chat to a specific location or state within the external resource. Within a given external resource, response messages can be sent to users on the messaging client 104. The external resource can selectively include different media items in the responses, based on a current context of the external resource.

The messaging client 104 can present a list of the available external resources (e.g., applications 106 or applets) to a user to launch or access a given external resource. This list can be presented in a context-sensitive menu. For example, the icons representing different ones of the application 106 (or applets) can vary based on how the menu is launched by the user (e.g., from a conversation interface or from a non-conversation interface).

Figure 2:
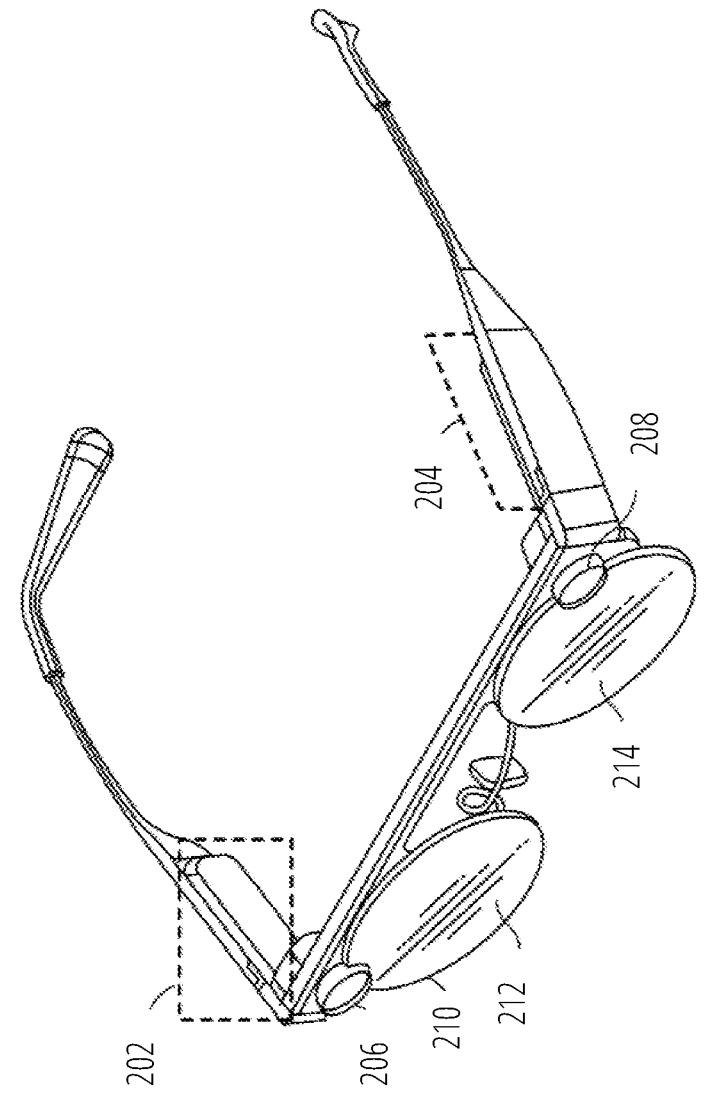
FIG. 2 illustrates a head-wearable apparatus, according to one example embodiment.

FIG. 2 illustrates a head-wearable apparatus 200, according to one example embodiment. FIG. 2 illustrates a perspective view of the head-wearable apparatus 200 according to one example embodiment. In some examples, the client device 102 may include the head-wearable apparatus 200. In some examples, the head-wearable apparatus may be part of the messaging server system 108.

In FIG. 2, the head-wearable apparatus 200 is a pair of eyeglasses. In some embodiments, the head-wearable apparatus 200 can be sunglasses or goggles. Some embodiments can include one or more wearable devices, such as a pendant with an integrated camera that is integrated with, in communication with, or coupled to, the head-wearable apparatus 200 or a client device 102. Any desired wearable device may be used in conjunction with the embodiments of the present disclosure, such as a watch, a headset, a wristband, earbuds, clothing (such as a hat or jacket with integrated electronics), a clip-on electronic device, or any other wearable devices. It is understood that, while not shown, one or more portions of the system included in the head-wearable apparatus 200 can be included in a client device 102 that can be used in conjunction with the head-wearable apparatus 200.

In FIG. 2, the head-wearable apparatus 200 is a pair of eyeglasses that includes a frame 210 that includes eye wires (or rims) that are coupled to two stems (or temples), respectively, via hinges and/or end pieces. The eye wires of the frame 210 carry or hold a pair of lenses (e.g., lens 212 and lens 214). The frame 210 includes a first (e.g., right) side that is coupled to the first stem and a second (e.g., left) side that is coupled to the second stem. The first side is opposite the second side of the frame 210. The pair of lenses (e.g., lens 212 and lens 214) may be flexible lenses. Further details of the flexible lenses are provided below in connection with FIG. 3.

The head-wearable apparatus 200 further includes a camera module (not shown) that includes camera lenses (e.g., camera lens 206, camera lens 208) and at least one image sensor. The camera lens 206 and camera lens 208 may be a perspective camera lens or a non-perspective camera lens. A non-perspective camera lens may be, for example, a fisheye lens, a wide-angle lens, an omnidirectional lens, etc. The image sensor captures digital video through the camera lens 206 and camera lens 208. The images may also be still image frame or a video including a plurality of still image frames. The camera module can be coupled to the frame 210. As shown in FIG. 2 the frame 210 is coupled to the camera lens 206 and camera lens 208 such that the camera lenses (e.g., camera lens 206, camera lens 208) face forward. The camera lens 206 and camera lens 208 can be perpendicular to the lens 212 and lens 214. The camera module can include dual-front facing cameras that are separated by the width of the frame 210 or the width of the head of the user of the head-wearable apparatus 200.

In FIG. 2, the two stems (or temples) are respectively coupled to microphone housing 202 and microphone housing 204. The first and second stems are coupled to opposite sides of a frame 210 of the head-wearable apparatus 200. The first stem is coupled to the first microphone housing 202 and the second stem is coupled to the second microphone housing 204. The microphone housing 202 and microphone housing 204 can be coupled to the stems between the locations of the frame 210 and the temple tips. The microphone housing 202 and microphone housing 204 can be located on either side of the user's temples when the user is wearing the head-wearable apparatus 200.

As shown in FIG. 2, the microphone housing 202 and microphone housing 204 encase a plurality of microphones (not shown). The microphones are air interface sound pickup devices that convert sound into an electrical signal. More specifically, the microphones are transducers that convert acoustic pressure into electrical signals (e.g., acoustic signals). Microphones can be digital or analog microelectro-mechanical systems (MEMS) microphones. The acoustic signals generated by the microphones can be pulse density modulation (PDM) signals.

Figure 3:
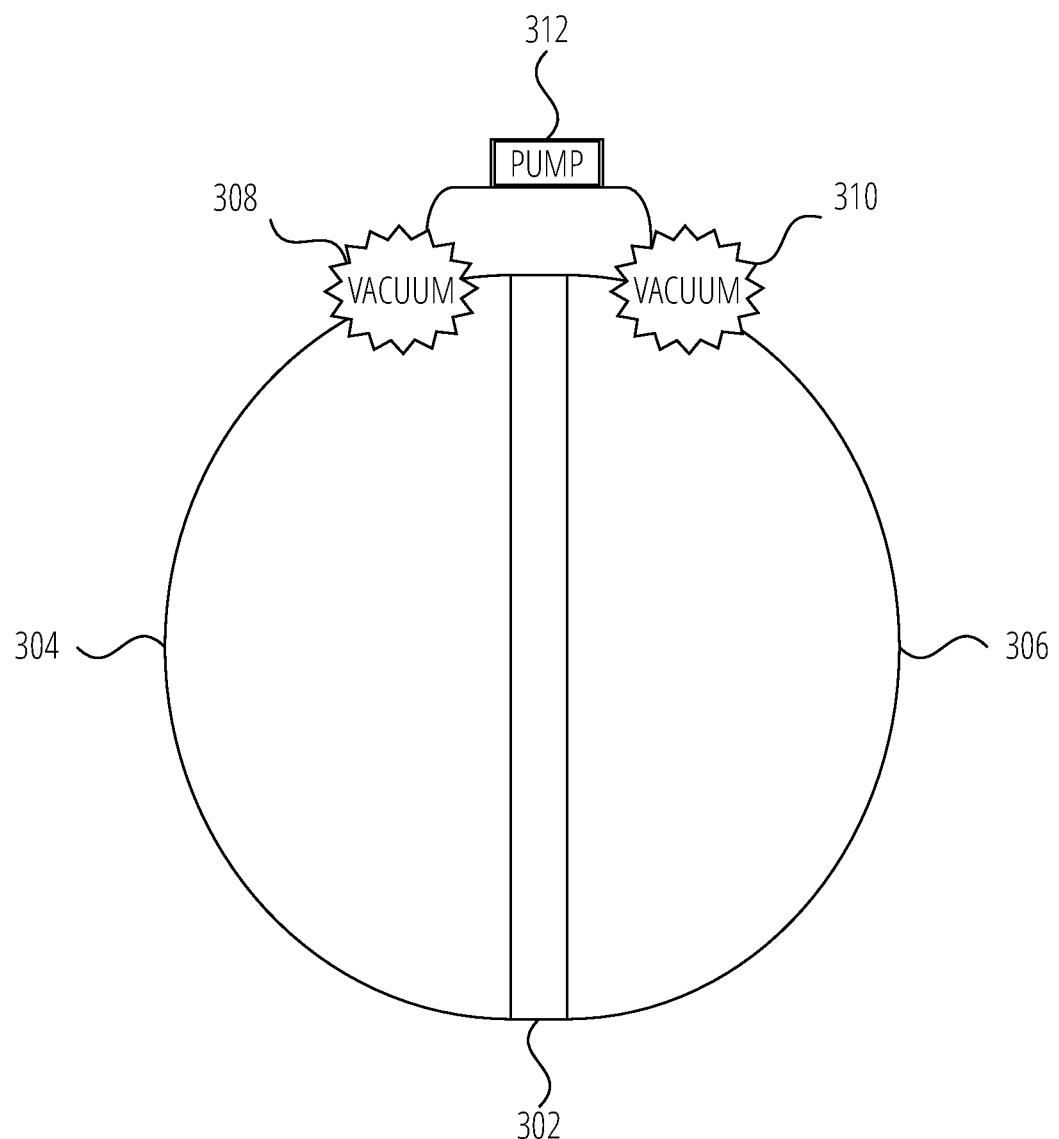
FIG. 3 is an illustration of an example flexible lens of a head-wearable apparatus, according to example embodiments.

FIG. 3 is an illustration of an example flexible lens of a head-wearable apparatus 200. The illustration in FIG. 3 depicts an example eyeglass lens that can be used in lens 212 and lens 214. The flexible lens is shown to include a front soft lens 304 and a back soft lens 306. The soft lenses 304 and 306 are separated by a hard lens 302. The soft lenses 304 and 306 may be made of a flexible material. The flexible material must have the ability to bend. In some examples the flexible material is a flexible or soft plastic. The hard lens 302 is a flat glass. The material of the hard lens 302 cannot bend light. Example materials of the hard lens 302 include but are not limited to: clear glass, polycarbonate, and high-index plastics.

The flexible lens depicted in FIG. 3 additionally includes of a pump and vacuum system. The pump and vacuum system includes a pump 312, vacuum 308 and vacuum 310. The pump 312 may be physically coupled to an air tank (not pictured). In some examples, the pump 312 is further coupled to an air filter (not pictured) that purifies that air from the air tank. In some examples, the head-wearable apparatus 200 includes a pump 312 on each flexible lens (e.g., lens 212 and lens 214). In another example, the head-wearable apparatus 200 includes a single pump 312 that is physically attached to the frame 210.

The volume between the front soft lens 304 and the hard lens 302 may be referred to herein as the front curvature of a lens. The volume between the hard lens 302 and the back soft lens 306 may referred to as the back curvature of the lens.

In some examples, the flexible lens depicted in FIG. 3 additionally includes a motor. The motor can move the position of the lens relative to the head-wearable apparatus. Each flexible lens in the head-wearable apparatus may contain an individual motor.

Although the described flow diagram below can show operations as a sequential process, many of the operations can be performed in parallel or concurrently. In addition, the order of the operations may be re-arranged. A process is terminated when its operations are completed. A process may correspond to a method, a procedure, an algorithm, etc. The operations of methods may be performed in whole or in part, may be performed in conjunction with some or all of the operations in other methods, and may be performed by any number of different systems, such as the systems described herein, or any portion thereof, such as a processor included in any of the systems.

FIG. 4 is a method 400 for remotely adjusting the prescription of a pair of wearable eyeglasses, according to example embodiments. In one example, the processor in client device 102, the processor in a head-wearable apparatus, the processor in the messaging server system 108, the processor in the prescription system 130, or any combination thereof, can perform the operations in the method 400.

In some examples, an operator of a client device 102 remotely a head-wearable apparatus 200 using the operations described in the method 400. The client device 102 may include a desktop computer or mobile computing device. Each of the client device 102 and the head-wearable apparatus 200 may include the prescription system 130. The operator of the client device 102 may be an optometrist and a wearer of the head-wearable apparatus 200 may be a patient.

At operation 402, the prescription system 130 receives a current state of a pair of lenses affixed to a head-wearable apparatus. The head-wearable apparatus may be the head-wearable apparatus 200. The pair of lenses may be flexible lenses as described in connection with FIGS. 2-3. The current state of the pair of lenses may reflect the current curvature of each of the lenses. The curvature of the lenses may be received by at least one of a spherometer and a set of pressure gauges that are affixed to the head-wearable apparatus 200.

At operation 404, the prescription system 130 causes presentation of one or more images on a graphical user interface displayed on the pair of lenses. The one or more images may be augmented reality images.

At operation 406, the prescription system 130 receives, from a microphone coupled to the head-wearable apparatus 200, audio feedback relating to the one or more images. The audio feedback may be provided by a wearer of the head-wearable apparatus 200. The wearer may indicate that the one or images are too blurry or are clear. The prescription system 130 may record the audio feedback and transmit the audio feedback via a network 112 to one or more client devices 102.

In some examples, the feedback may be received from a camera system coupled to the head-wearable apparatus 200 (e.g., camera lens 206, camera lens 208). For examples, a wearer of the head-wearable apparatus 200 may provide one or more hand gestures in front of the camera system. The prescription system 130 may record the hand gestures and transmit the recorded video via a network 112 to one or more client devices 102.

At operation 408, based on the feedback, the prescription system 130 sends an instruction to cause an air pump affixed to the head-wearable apparatus 200 to inflate one or more compartments of the pair of lenses. The one or more compartments comprises at least one of a front curvature and a back curvature. The front curvature is the volume between the front soft lens 304 and the hard lens 302. The back curvature is the volume between the hard lens 302 and the back soft lens 306.

Each lens in the pair of lenses of the head-wearable apparatus 200 includes a vacuum system. For example, a first lens in the pair of lenses comprises a first vacuum system and a second lens in the pair of lenses comprises a second vacuum system. The first vacuum system and the second vacuum system are physically coupled to the air pump. The air pump is physically attached to a frame 210 of the head-wearable apparatus 200. Further details of the vacuum systems are provided above in connection with FIG. 3.

At operation 410, in response to the instruction, the prescription system 130 receives an updated state of the pair of lenses. The updated state of the pair of lenses may reflect the updated curvature of each of the lenses. The curvature of the lenses may be received by at least one of a spherometer and a set of pressure gauges that are affixed to the head-wearable apparatus 200.

At operation 412, the prescription system 130 generates prescription data for the pair of lenses based on the updated state of the pair of lenses. For example, the prescription system 130 converts the air pressure measurements of each lens in the pair of lenses into prescription data.

In some examples, the prescription system 130 generates updated images. The updated images are generated by modifying the one or more images based on the updated state of the pair of lenses. The prescription system 130 causes presentation of the updated images on the graphical user interface displayed on the pair of lenses.

Figure 5:
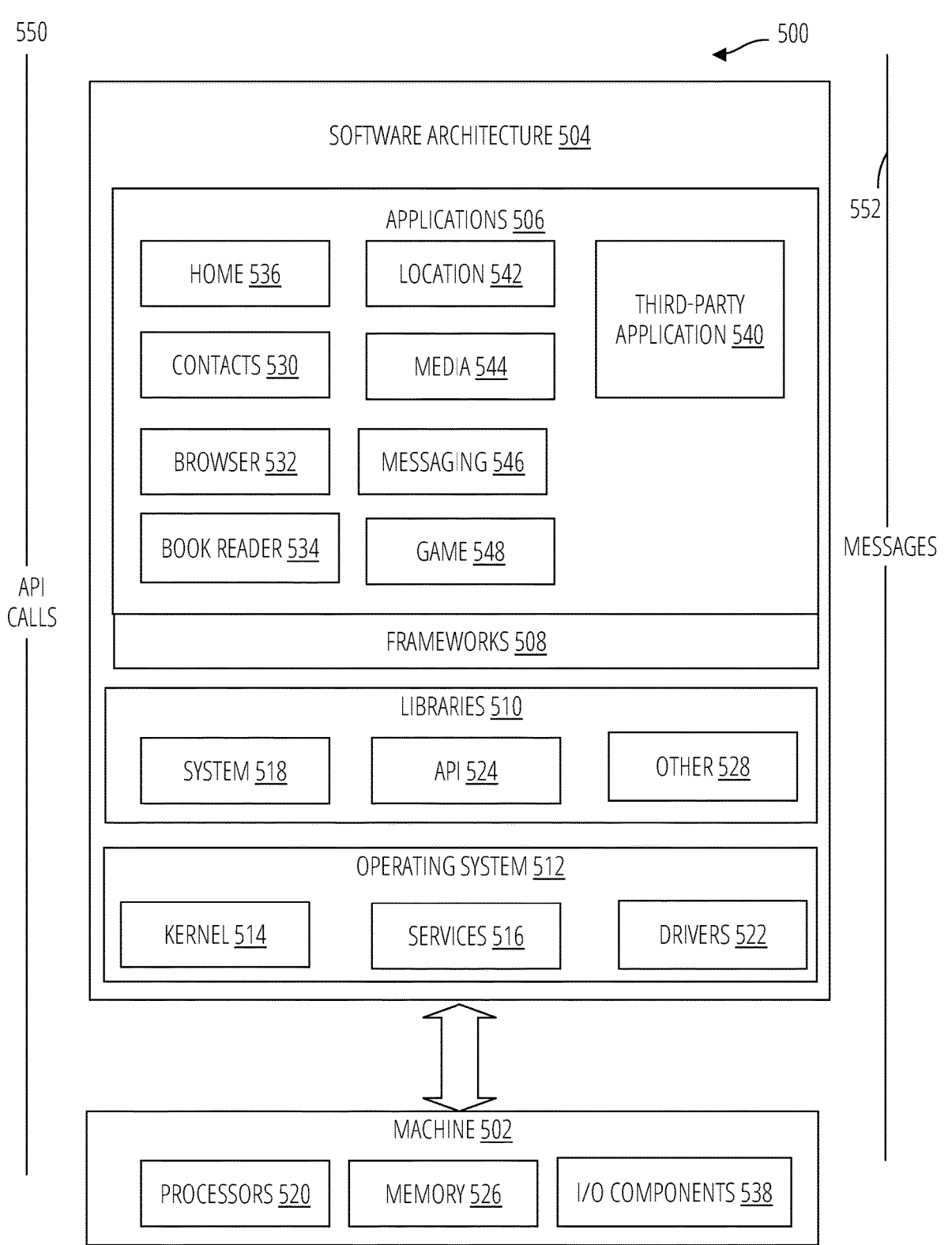
FIG. 5 is a block diagram illustrating a software architecture, which can be installed on any one or more of the devices described herein

FIG. 5 is a block diagram 500 illustrating a software architecture 504, which can be installed on any one or more of the devices described herein. The software architecture 504 is supported by hardware such as a machine 502 that includes processors 520, memory 526, and I/O components 538. In this example, the software architecture 504 can be conceptualized as a stack of layers, where each layer provides a particular functionality. The software architecture 504 includes layers such as an operating system 512, libraries 510, frameworks 508, and applications 506. Operationally, the applications 506 invoke API calls 550 through the software stack and receive messages 552 in response to the API calls 550.

The operating system 512 manages hardware resources and provides common services. The operating system 512 includes, for example, a kernel 514, services 516, and drivers 522. The kernel 514 acts as an abstraction layer between the hardware and the other software layers. For example, the kernel 514 provides memory management, processor management (e.g., scheduling), component management, networking, and security settings, among other functionalities. The services 516 can provide other common services for the other software layers. The drivers 522 are responsible for controlling or interfacing with the underlying hardware. For instance, the drivers 522 can include display drivers, camera drivers, BLUETOOTH® or BLUETOOTH® Low Energy drivers, flash memory drivers, serial communication drivers (e.g., Universal Serial Bus (USB) drivers), WI-FI® drivers, audio drivers, power management drivers, and so forth.

The libraries 510 provide a low-level common infrastructure used by the applications 506. The libraries 510 can include system libraries 518 (e.g., C standard library) that provide functions such as memory allocation functions, string manipulation functions, mathematic functions, and the like. In addition, the libraries 510 can include API libraries 524 such as media libraries (e.g., libraries to support presentation and manipulation of various media formats such as Moving Picture Experts Group-4 (MPEG4), Advanced Video Coding (H.264 or AVC), Moving Picture Experts Group Layer-3 (MP3), Advanced Audio Coding (AAC), Adaptive Multi-Rate (AMR) audio codec, Joint Photographic Experts Group (JPEG or JPG), or Portable Network Graphics (PNG)), graphics libraries (e.g., an OpenGL framework used to render in two dimensions (2D) and three dimensions (3D) in a graphic content on a display), database libraries (e.g., SQLite to provide various relational database functions), web libraries (e.g., WebKit to provide web browsing functionality), and the like. The libraries 510 can also include a wide variety of other libraries 528 to provide many other APIs to the applications 506.

The frameworks 508 provide a high-level common infrastructure that is used by the applications 506. For example, the frameworks 508 provide various graphical user interface (GUI) functions, high-level resource management, and high-level location services. The frameworks 508 can provide a broad spectrum of other APIs that can be used by the applications 506, some of which may be specific to a particular operating system or platform.

In an example embodiment, the applications 506 may include a home application 536, a contacts application 530, a browser application 532, a book reader application 534, a location application 542, a media application 544, a messaging application 546, a game application 548, and a broad assortment of other applications such as a third-party application 540. The applications 506 are programs that execute functions defined in the programs. Various programming languages can be employed to create one or more of the applications 506, structured in a variety of manners, such as object-oriented programming languages (e.g., Objective-C, Java, or C++) or procedural programming languages (e.g., C or assembly language). In a specific example, the third-party application 540 (e.g., an application developed using the ANDROID™ or IOS™ software development kit (SDK) by an entity other than the vendor of the particular platform) may be mobile software running on a mobile operating system such as IOS™, ANDROID™, WINDOWS® Phone, or another mobile operating system. In this example, the third-party application 540 can invoke the API calls 550 provided by the operating system 512 to facilitate functionality described herein.

Figure 6:
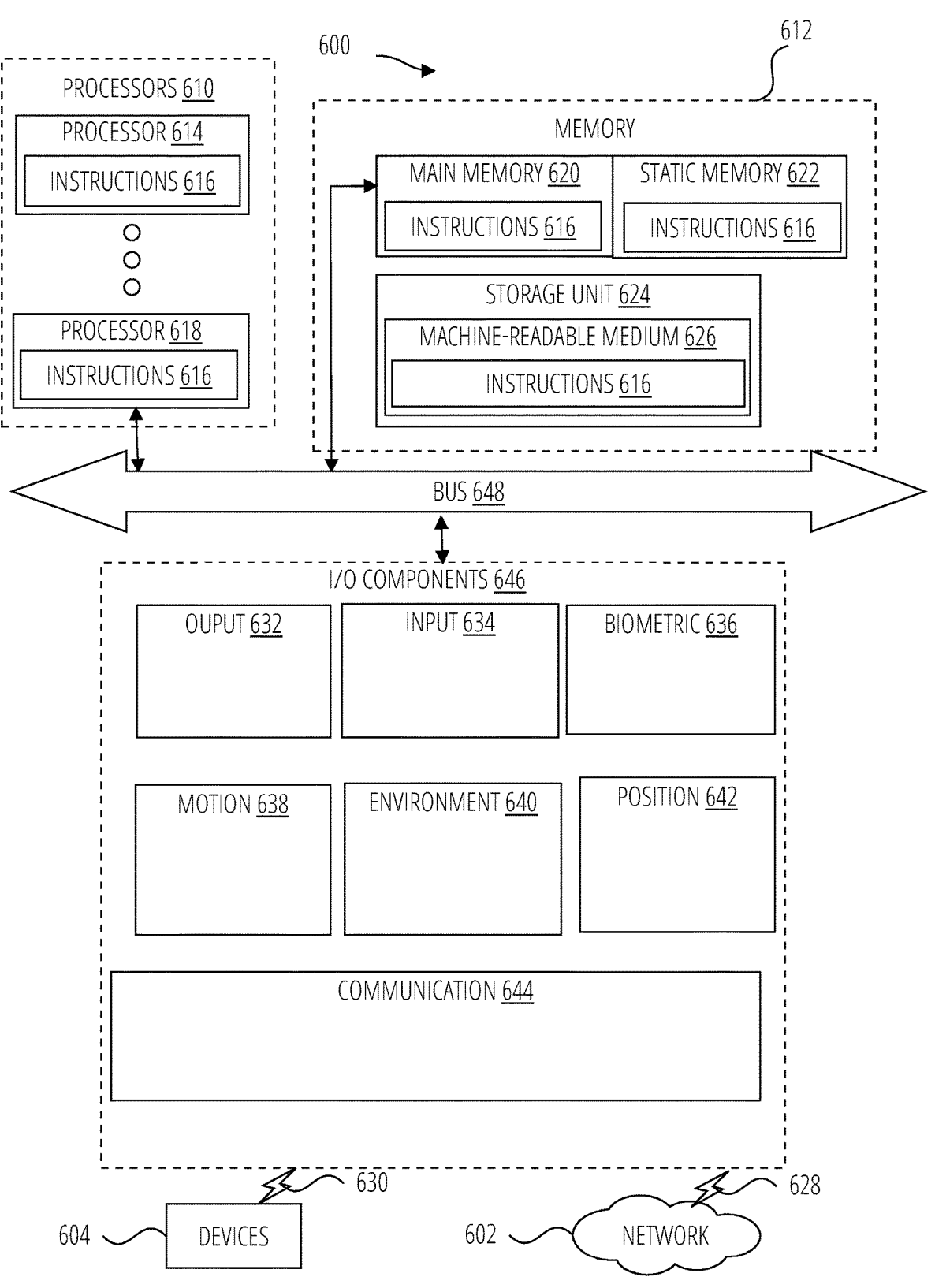
FIG. 6 is a diagrammatic representation of the machine within which instructions for causing the machine to perform any one or more of the methodologies discussed herein may be executed.

FIG. 6 is a diagrammatic representation of the machine 600 within which instructions 616 (e.g., software, a program, an application, an applet, an app, or other executable code) for causing the machine 600 to perform any one or more of the methodologies discussed herein may be executed. For example, the instructions 616 may cause the machine 600 to execute any one or more of the methods described herein. The instructions 616 transform the general, non-programmed machine 600 into a particular machine 600 programmed to carry out the described and illustrated functions in the manner described. The machine 600 may operate as a standalone device or may be coupled (e.g., networked) to other machines. In a networked deployment, the machine 600 may operate in the capacity of a server machine or a client machine in a server-client network environment, or as a peer machine in a peer-to-peer (or distributed) network environment. The machine 600 may comprise, but not be limited to, a server computer, a client computer, a personal computer (PC), a tablet computer, a laptop computer, a netbook, a set-top box (STB), a PDA, an entertainment media system, a cellular telephone, a smart phone, a mobile device, a wearable device (e.g., a smart watch), a smart home device (e.g., a smart appliance), other smart devices, a web appliance, a network router, a network switch, a network bridge, or any machine capable of executing the instructions 616, sequentially or otherwise, that specify actions to be taken by the machine 600. Further, while only a single machine 600 is illustrated, the term "machine" shall also be taken to include a collection of machines that individually or jointly execute the instructions 616 to perform any one or more of the methodologies discussed herein.

The machine 600 may include processors 610, memory 612, and I/O components 646, which may be configured to communicate with each other via a bus 648. In an example embodiment, the processors 610 (e.g., a Central Processing Unit (CPU), a Reduced Instruction Set Computing (RISC) processor, a Complex Instruction Set Computing (CISC) processor, a Graphics Processing Unit (GPU), a Digital Signal Processor (DSP), an ASIC, a Radio-Frequency Integrated Circuit (RFIC), another processor, or any suitable combination thereof) may include, for example, a processor 614 and a processor 618 that execute the instructions 616. The term "processor" is intended to include multi-core processors that may comprise two or more independent processors (sometimes referred to as "cores") that may execute instructions contemporaneously. Although FIG. 6 shows multiple processors 610, the machine 600 may include a single processor with a single core, a single processor with multiple cores (e.g., a multi-core processor), multiple processors with a single core, multiple processors with multiples cores, or any combination thereof.

The memory 612 includes a main memory 620, a static memory 622 and a storage unit 624 both accessible to the processors 610 via the bus 648. The main memory 620, the static memory 622, and storage unit 624 store the instructions 616 embodying any one or more of the methodologies or functions described herein. The instructions 616 may also reside, completely or partially, within the main memory 620 within the static memory 622, within machine-readable medium 626 within the storage unit 624, within at least one of the processors 610 (e.g., within the processor's cache memory), or any suitable combination thereof, during execution thereof by the machine 600.

The I/O components 646 may include a wide variety of components to receive input, provide output, produce output, transmit information, exchange information, capture measurements, and so on. The specific I/O components 646 that are included in a particular machine will depend on the type of machine. For example, portable machines such as mobile phones may include a touch input device or other such input mechanisms, while a headless server machine will likely not include such a touch input device. It will be appreciated that the I/O components 646 may include many other components that are not shown in FIG. 6. In various example embodiments, the I/O components 646 may include output components 632 and input components 634. The output components 632 may include visual components (e.g., a display such as a plasma display panel (PDP), a light emitting diode (LED) display, a liquid crystal display (LCD), a projector, or a cathode ray tube (CRT)), acoustic components (e.g., speakers), haptic components (e.g., a vibratory motor, resistance mechanisms), other signal generators, and so forth. The input components 634 may include alphanumeric input components (e.g., a keyboard, a touch screen configured to receive alphanumeric input, a photo-optical keyboard, or other alphanumeric input components), point-based input components (e.g., a mouse, a touchpad, a trackball, a joystick, a motion sensor, or another pointing instrument), tactile input components (e.g., a physical button, a touch screen that provides location and/or force of touches or touch gestures, or other tactile input components), audio input components (e.g., a microphone), and the like.

In further example embodiments, the I/O components 646 may include biometric components 636, motion components 638, environmental components 640, or position components 642, among a wide array of other components. For example, the biometric components 636 include components to detect expressions (e.g., hand expressions, facial expressions, vocal expressions, body gestures, or eye tracking), measure biosignals (e.g., blood pressure, heart rate, body temperature, perspiration, or brain waves), identify a person (e.g., voice identification, retinal identification, facial identification, fingerprint identification, or electroencephalogram-based identification), and the like. The motion components 638 include acceleration sensor components (e.g., accelerometer), gravitation sensor components, rotation sensor components (e.g., gyroscope), and so forth. The environmental components 640 include, for example, illumination sensor components (e.g., photometer), temperature sensor components (e.g., one or more thermometers that detect ambient temperature), humidity sensor components, pressure sensor components (e.g., barometer), acoustic sensor components (e.g., one or more microphones that detect background noise), proximity sensor components (e.g., infrared sensors that detect nearby objects), gas sensors (e.g., gas detection sensors to detection concentrations of hazardous gases for safety or to measure pollutants in the atmosphere), or other components that may provide indications, measurements, or signals corresponding to a surrounding physical environment. The position components 642 include location sensor components (e.g., a GPS receiver component), altitude sensor components (e.g., altimeters or barometers that detect air pressure from which altitude may be derived), orientation sensor components (e.g., magnetometers), and the like.

Communication may be implemented using a wide variety of technologies. The I/O components 646 further include communication components 644 operable to couple the machine 600 to a network 602 or devices 604 via respective couplings or connections, respectively. For example, the communication components 644 may include a network interface component or another suitable device to interface with the network 602. In further examples, the communication components 644 may include wired communication components, wireless communication components, cellular communication components, Near Field Communication (NFC) components, Bluetooth® components (e.g., Bluetooth® Low Energy), WiFi® components, and other communication components to provide communication via other modalities. The devices 604 may be another machine or any of a wide variety of peripheral devices (e.g., a peripheral device coupled via a USB).

Moreover, the communication components 644 may detect identifiers or include components operable to detect identifiers. For example, the communication components 644 may include Radio Frequency Identification (RFID) tag reader components, NFC smart tag detection components, optical reader components (e.g., an optical sensor to detect one-dimensional bar codes such as Universal Product Code (UPC) bar code, multi-dimensional bar codes such as Quick Response (QR) code, Aztec code, Data Matrix, Dataglyph, MaxiCode, PDF417, Ultra Code, UCC RSS-2D bar code, and other optical codes), or acoustic detection components (e.g., microphones to identify tagged audio signals). In addition, a variety of information may be derived via the communication components 644, such as location via Internet Protocol (IP) geolocation, location via Wi-Fi® signal triangulation, location via detecting an NFC beacon signal that may indicate a particular location, and so forth.

The various memories (e.g., memory 612, main memory 620, static memory 622 and/or memory of the processors 610) and/or storage unit 624 may store one or more sets of instructions and data structures (e.g., software) embodying or used by any one or more of the methodologies or functions described herein. These instructions (e.g., the instructions 616), when executed by processors 610, cause various operations to implement the disclosed embodiments.

The instructions 616 may be transmitted or received over the network 602, using a transmission medium, via a network interface device (e.g., a network interface component included in the communication components 644) and using any one of a number of well-known transfer protocols (e.g., hypertext transfer protocol (HTTP)). Similarly, the instructions 616 may be transmitted or received using a transmission medium via the coupling 606 (e.g., a peer-to-peer coupling) to the devices 604.

"Computer-readable storage medium" refers to both machine-storage media and transmission media. Thus, the terms include both storage devices/media and carrier waves/modulated data signals. The terms "machine-readable medium," "computer-readable medium" and "device-readable medium" mean the same thing and may be used interchangeably in this disclosure.

"Machine storage medium" refers to a single or multiple storage devices and media (e.g., a centralized or distributed database, and associated caches and servers) that store executable instructions, routines and data. The term shall accordingly be taken to include, but not be limited to, solid-state memories, and optical and magnetic media, including memory internal or external to processors. Specific examples of machine-storage media, computer-storage media and device-storage media include non-volatile memory, including by way of example semiconductor memory devices, e.g., erasable programmable read-only memory (EPROM), electrically erasable programmable read-only memory (EEPROM), FPGA, and flash memory devices; magnetic disks such as internal hard disks and removable disks; magneto-optical disks; and CD-ROM and DVD-ROM disks The terms "machine-storage medium," "device-storage medium," "computer-storage medium" mean the same thing and may be used interchangeably in this disclosure. The terms "machine-storage media," "computer-storage media," and "device-storage media" specifically exclude carrier waves, modulated data signals, and other such media, at least some of which are covered under the term "signal medium."

"Non-transitory computer-readable storage medium" refers to a tangible medium that is capable of storing, encoding, or carrying the instructions for execution by a machine.

"Signal medium" refers to any intangible medium that is capable of storing, encoding, or carrying the instructions for execution by a machine and includes digital or analog communications signals or other intangible media to facilitate communication of software or data. The term "signal medium" shall be taken to include any form of a modulated data signal, carrier wave, and so forth. The term "modulated data signal" means a signal that has one or more of its characteristics set or changed in such a matter as to encode information in the signal. The terms "transmission medium" and "signal medium" mean the same thing and may be used interchangeably in this disclosure.

System with Head-Wearable Apparatus

Figure 7:
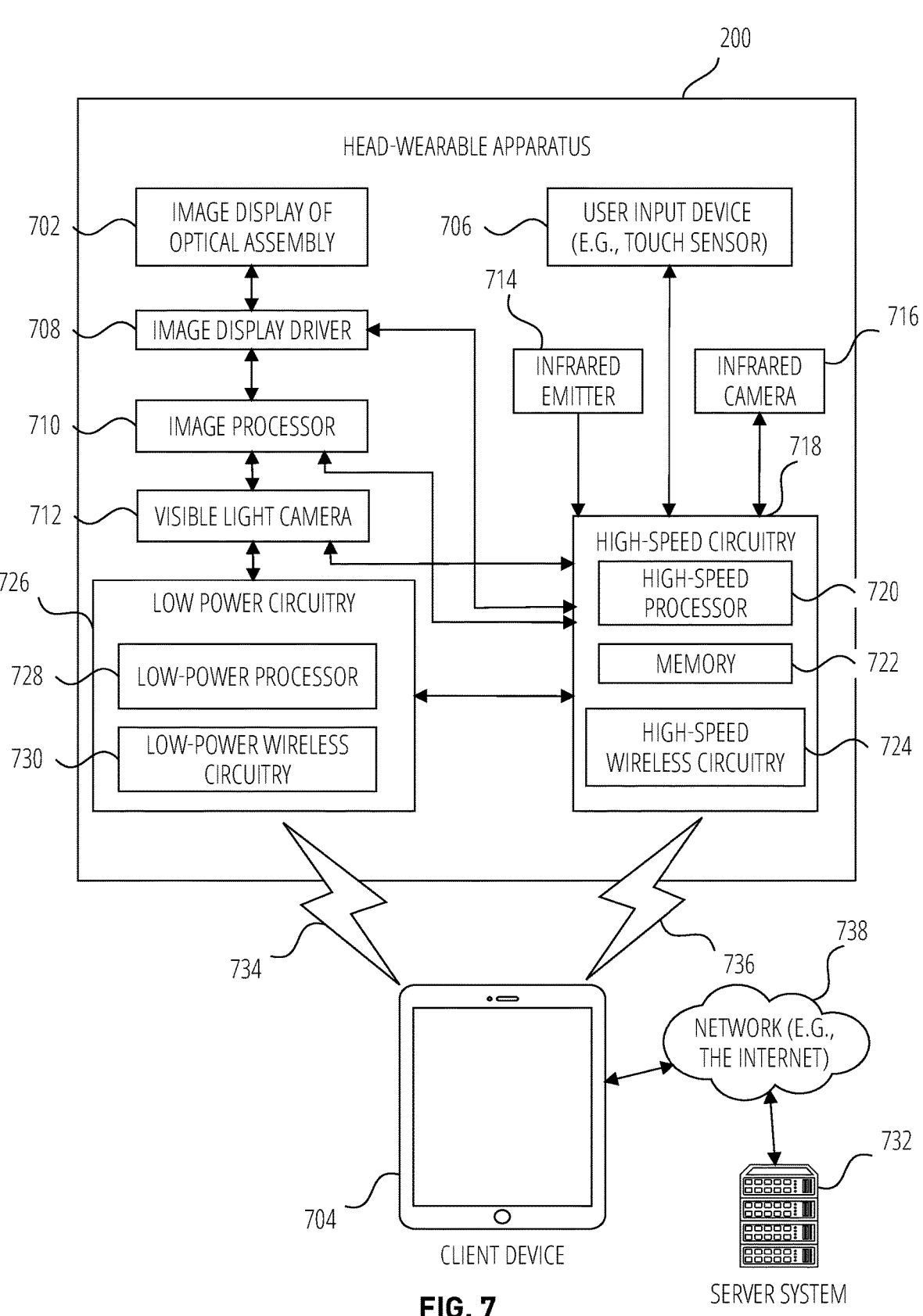
FIG. 7 illustrates a system in which the head-wearable apparatus can be implemented according to one example embodiment.

FIG. 7 illustrates a system in which the head-wearable apparatus 200 can be implemented according to one example embodiment. FIG. 7 is a high-level functional block diagram of an example head-wearable apparatus 200 communicatively coupled a mobile client device 102 (or client device 704 as shown in FIG. 7) and a server system 732 via various network 738.

Head-wearable apparatus 200 includes a camera, such as at least one of visible light camera 712, infrared emitter 714 and infrared camera 716. The camera can include the camera module with the camera lens 206 and camera lens 208 in FIG. 2.

Client device 102 can be capable of connecting with head-wearable apparatus 200 using both a low-power wireless connection 734 and a high-speed wireless connection 736. Client device 102 is connected to server system 732 and network 738. The network 738 may include any combination of wired and wireless connections.

Head-wearable apparatus 200 further includes two image displays of the image display of optical assembly 702. The two image displays image display of optical assembly 702 include one associated with the left lateral side and one associated with the right lateral side of the head-wearable apparatus 200. Head-wearable apparatus 200 also includes image display driver 708, image processor 710, low-power low power circuitry 726, and high-speed circuitry 718. Image display of optical assembly 702 are for presenting images and videos, including an image that can include a graphical user interface to a user of the head-wearable apparatus 200.

Image display driver 708 commands and controls the image display of the image display of optical assembly 702. Image display driver 708 may deliver image data directly to the image display of the image display of optical assembly 702 for presentation or may have to convert the image data into a signal or data format suitable for delivery to the image display device. For example, the image data may be video data formatted according to compression formats, such as H. 264 (MPEG-4 Part 10), HEVC, Theora, Dirac, RealVideo RV40, VP8, VP9, or the like, and still image data may be formatted according to compression formats such as Portable Network Group (PNG), Joint Photographic Experts Group (JPEG), Tagged Image File Format (TIFF) or exchangeable image file format (Exif) or the like.

As noted above, head-wearable apparatus 200 includes a frame 210 and stems (or temples) extending from a lateral side of the frame 210. Head-wearable apparatus 200 further includes a user input device 706 (e.g., touch sensor or push button) including an input surface on the head-wearable apparatus 200. The user input device 706 (e.g., touch sensor or push button) is to receive from the user an input selection to manipulate the graphical user interface of the presented image.

The components shown in FIG. 7 for the head-wearable apparatus 200 are located on one or more circuit boards, for example a PCB or flexible PCB, in the rims or temples. Alternatively or additionally, the depicted components can be located in the chunks, frames, hinges, or bridge of the head-wearable apparatus 200. Left and right visible light cameras 712 can include digital camera elements such as a complementary metal-oxide-semiconductor (CMOS) image sensor, charge coupled device, a camera lens 206 and camera lens 208, or any other respective visible or light capturing elements that may be used to capture data, including images of scenes with unknown objects.

Head-wearable apparatus 200 includes a memory 722 which stores instructions to perform a subset or all of the functions described herein. Memory 722 can also include storage device.

As shown in FIG. 7, high-speed circuitry 718 includes high-speed processor 720, memory 722, and high-speed wireless circuitry 724. In the example, the image display driver 708 is coupled to the high-speed circuitry 718 and operated by the high-speed processor 720 in order to drive the left and right image displays of the image display of optical assembly 702. High-speed processor 720 may be any processor capable of managing high-speed communications and operation of any general computing system needed for head-wearable apparatus 200. High-speed processor 720 includes processing resources needed for managing high-speed data transfers on high-speed wireless connection 736 to a wireless local area network (WLAN) using high-speed wireless circuitry 724. In certain examples, the high-speed processor 720 executes an operating system such as a LINUX operating system or other such operating system of the head-wearable apparatus 200 and the operating system is stored in memory 722 for execution. In addition to any other responsibilities, the high-speed processor 720 executing a software architecture for the head-wearable apparatus 200 is used to manage data transfers with high-speed wireless circuitry 724. In certain examples, high-speed wireless circuitry 724 is configured to implement Institute of Electrical and Electronic Engineers (IEEE) 802.11 communication standards, also referred to herein as Wi-Fi. In other examples, other high-speed communications standards may be implemented by high-speed wireless circuitry 724.

Low-power wireless circuitry 730 and the high-speed wireless circuitry 724 of the head-wearable apparatus 200 can include short range transceivers (Bluetooth™) and wireless wide, local, or wide area network transceivers (e.g., cellular or WiFi). Client device 102, including the transceivers communicating via the low-power wireless connection 734 and high-speed wireless connection 736, may be implemented using details of the architecture of the head-wearable apparatus 200, as can other elements of network 738.

Memory 722 includes any storage device capable of storing various data and applications, including, among other things, camera data generated by the left and right visible light cameras 712, infrared camera 716, and the image processor 710, as well as images generated for display by the image display driver 708 on the image displays of the image display of optical assembly 702. While memory 722 is shown as integrated with high-speed circuitry 718, in other examples, memory 722 may be an independent standalone element of the head-wearable apparatus 200. In certain such examples, electrical routing lines may provide a connection through a chip that includes the high-speed processor 720 from the image processor 710 or low-power processor 728 to the memory 722. In other examples, the high-speed processor 720 may manage addressing of memory 722 such that the low-power processor 728 will boot the high-speed processor 720 any time that a read or write operation involving memory 722 is needed.

As shown in FIG. 7, the low-power processor 728 or high-speed processor 720 of the head-wearable apparatus 200 can be coupled to the camera (visible light camera 712; infrared emitter 714, or infrared camera 716), the image display driver 708, the user input device 706 (e.g., touch sensor or push button), and the memory 722.

Head-wearable apparatus 200 is connected with a host computer. For example, the head-wearable apparatus 200 is paired with the client device 102 via the high-speed wireless connection 736 or connected to the server system 732 via the network 738. Server system 732 may be one or more computing devices as part of a service or network computing system, for example, that include a processor, a memory, and network communication interface to communicate over the network 738 with the client device 102 and head-wearable apparatus 200.

The client device 102 includes a processor and a network communication interface coupled to the processor. The network communication interface allows for communication over the network 738, low-power wireless connection 734 or high-speed wireless connection 736. Client device 102 can further store at least portions of the instructions for generating a binaural audio content in the client device 102's memory to implement the functionality described herein.

Output components of the head-wearable apparatus 200 include visual components, such as a display such as a liquid crystal display (LCD), a plasma display panel (PDP), a light emitting diode (LED) display, a projector, or a waveguide. The image displays of the optical assembly are driven by the image display driver 708. The output components of the head-wearable apparatus 200 further include acoustic components (e.g., speakers), haptic components (e.g., a vibratory motor), other signal generators, and so forth. The input components of the head-wearable apparatus 200, the client device 102, and server system 732, such as the user input device 706, may include alphanumeric input components (e.g., a keyboard, a touch screen configured to receive alphanumeric input, a photo-optical keyboard, or other alphanumeric input components), point-based input components (e.g., a mouse, a touchpad, a trackball, a joystick, a motion sensor, or other pointing instruments), tactile input components (e.g., a physical button, a touch screen that provides location and force of touches or touch gestures, or other tactile input components), audio input components (e.g., a microphone), and the like.

Head-wearable apparatus 200 may optionally include additional peripheral device elements. Such peripheral device elements may include biometric sensors, additional sensors, or display elements integrated with head-wearable apparatus 200. For example, peripheral device elements may include any I/O components including output components, motion components, position components, or any other such elements described herein.

For example, the biometric components include components to detect expressions (e.g., hand expressions, facial expressions, vocal expressions, body gestures, or eye tracking), measure biosignals (e.g., blood pressure, heart rate, body temperature, perspiration, or brain waves), identify a person (e.g., voice identification, retinal identification, facial identification, fingerprint identification, or electroencephalogram based identification), and the like. The motion components include acceleration sensor components (e.g., accelerometer), gravitation sensor components, rotation sensor components (e.g., gyroscope), and so forth. The position components include location sensor components to generate location coordinates (e.g., a Global Positioning System (GPS) receiver component), WiFi or Bluetooth™ transceivers to generate positioning system coordinates, altitude sensor components (e.g., altimeters or barometers that detect air pressure from which altitude may be derived), orientation sensor components (e.g., magnetometers), and the like. Such positioning system coordinates can also be received over low-power wireless connections 734 and high-speed wireless connection 736 from the client device 102 via the low-power wireless circuitry 730 or high-speed wireless circuitry 724.

Where a phrase similar to "at least one of A, B, or C," "at least one of A, B, and C," "one or more A, B, or C," or "one or more of A, B, and C" is used, it is intended that the phrase be interpreted to mean that A alone may be present in an embodiment, B alone may be present in an embodiment, C alone may be present in an embodiment, or that any combination of the elements A, B and C may be present in a single embodiment; for example, A and B, A and C, B and C, or A and B and C.

Changes and modifications may be made to the disclosed embodiments without departing from the scope of the present disclosure. These and other changes or modifications are intended to be included within the scope of the present disclosure, as expressed in the following claims.

What is claimed is:

1. A method comprising:
receiving, by a processor, a current state of a pair of flexible lenses affixed to a head-wearable apparatus;
causing presentation of one or more augmented reality (AR) images on a graphical user interface displayed on the pair of lenses through an AR display system installed on the pair of lenses;
receiving, from a microphone coupled to the head-wearable apparatus, audio feedback relating to the one or more AR images;
based on the feedback, sending an instruction to cause an air pump affixed to the head-wearable apparatus to inflate one or more compartments of the pair of lenses until the user can see the AR images with a preferred level of clarity;
in response to the instruction, receiving an updated state of the pair of flexible lenses;
identifying curvature measurements of the updated state of the pair of flexible lenses using at least of one of a spherometer and a set of pressure gauges coupled to the head-wearable apparatus;
converting the curvature measurements of the flexible lenses into prescription data; and
generating prescription data for the pair of lenses based on the updated state of the pair of lenses, the prescription data being associated with prescription measurements for a second pair of lenses on a second pair of eyeglasses.

2. The method of claim 1, wherein the user provides feedback relating to the one or more AR images using hand gestures.

3. The method of claim 1, wherein the second pair of eyeglasses comprise of at least one non-flexible lens.

4. The method of claim 1, further comprising:
generating updated AR images, the updated AR images generated by modifying the one or more AR images based on the updated state of the pair of lenses; and
causing presentation of the updated AR images on the graphical user interface displayed on the pair of lenses.

5. The method of claim 1, wherein each lens of the of pair of flexible lenses comprises a front soft lens, a hard lens, and a back soft lens.

6. The method of claim 5, wherein the one or more compartments comprises at least one of a front curvature and a back curvature.

7. The method of claim 6, wherein the front curvature and the back curvature are separated by the hard lens.

8. The method of claim 6, wherein the front curvature is a volume between the front soft lens and the hard lens.

9. The method of claim 6, wherein the back curvature is a volume between the hard lens and the back soft lens.

10. The method of claim 1, wherein a first lens in the pair of lenses comprises a first vacuum system and a second lens in the pair of lenses comprises a second vacuum system.

11. The method of claim 10, wherein the first vacuum system and the second vacuum system are physically coupled to an air pump, the air pump being physically attached to a frame portion of the head-wearable apparatus.

12. A non-transitory computer-readable storage medium, the computer-readable storage medium including instructions that when executed by a computer, cause the computer to:

receive a current state of a pair of lenses affixed to a head-wearable apparatus;

cause presentation of one or more augmented reality (AR) images on a graphical user interface displayed on the pair of lenses through an AR display system installed on the pair of lenses;

receive, from a microphone coupled to the head-wearable apparatus, audio feedback relating to the one or more AR images;

based on the feedback, send an instruction to cause an air pump affixed to the head-wearable apparatus to inflate one or more compartments of the pair of lenses until the user can see the AR images with a preferred level of clarity;

in response to the instruction, receive an updated state of the pair of lenses;

identify curvature measurements of the updated state of the pair of flexible lenses using at least of one of a spherometer and a set of pressure gauges coupled to the head-wearable apparatus;

convert the curvature measurements of the flexible lenses into prescription data; and generate prescription data for the pair of lenses based on the updated state of the pair of lenses, the prescription data being associated with prescription measurements for a second pair of lenses on a second pair of eyeglasses.

13. The computer-readable storage medium of claim 12, wherein the user provides feedback relating to the one or more AR images using hand gestures.

14. The computer-readable storage medium of claim 12, wherein the instructions further configure the computer to:

generate updated AR images, the updated AR images generated by modifying the one or more AR images based on the updated state of the pair of lenses; and cause presentation of the updated AR images on the graphical user interface displayed on the pair of lenses.

15. The computer-readable storage medium of claim 12, wherein each lens of the of pair of flexible lenses comprises a front soft lens, a hard lens, and a back soft lens.

16. The computer-readable storage medium of claim 15, wherein the one or more compartments comprises at least one of a front curvature and a back curvature.

17. The computer-readable storage medium of claim 16, wherein the front curvature and the back curvature are separated by the hard lens.

18. The computer-readable storage medium of claim 16, wherein the front curvature is a volume between the front soft lens and the hard lens.

19. The computer-readable storage medium of claim 12, wherein a first lens in the pair of lenses comprises a first vacuum system and a second lens in the pair of lenses comprises a second vacuum system.

* * * * *